United States Patent

Dellinger

[11] 4,014,096
[45] Mar. 29, 1977

[54] METHOD AND APPARATUS FOR ORTHODONTIC TREATMENT

[76] Inventor: Eugene L. Dellinger, 1326 Old Lantern Trail, Fort Wayne, Ind. 46825

[22] Filed: Mar. 25, 1975

[21] Appl. No.: 561,697

[52] U.S. Cl. .............................................. 32/14 A
[51] Int. Cl.² ........................................... A61C 7/00
[58] Field of Search ......................... 32/14 A, 14 B

[56] References Cited

UNITED STATES PATENTS

| | | | |
|---|---|---|---|
| 3,738,005 | 6/1973 | Cohen et al. | 32/14 B |
| 3,787,976 | 1/1974 | Cohen | 32/14 A |
| 3,842,503 | 10/1974 | Wildman | 32/14 A |
| 3,871,098 | 3/1975 | Dean | 32/66 |

Primary Examiner—Robert Peshock
Attorney, Agent, or Firm—Gust, Irish, Jeffers & Rickert

[57] ABSTRACT

An idealized set of occluded models, both maxillae and mandible, containing castings of the patient's teeth is made with slotted brackets affixed thereto. The slots are oriented conjointly to define a single plane and a predetermined arch curvature which corresponds to the idealized dental arch. These brackets are placed on the patient's teeth in the same position as on the model, have affixed thereto during treatment one or more arch wires of prefabricated shape such that upon completion of the treatment the bracket slots will define a single plane and the aforesaid predetermined arch curvature which corresponds to the shape of the idealized dental arch. Once this slot pattern is achieved, the clinician knows that the treatment is completed.

31 Claims, 16 Drawing Figures

METHOD AND APPARATUS FOR ORTHODONTIC TREATMENT

BACKGROUND OF THE INVENTION

1. Field of the Invention

The present invention relates to orthodontics and more particularly to a method and apparatus for facilitating treatment.

2. Description of the Prior Art

In the practice of orthodontics, teeth are positionally corrected by means of an arch wire secured to certain teeth of a dental arch by means of brackets. This requires on the part of the practitioner considerable skill and judgment in the forming and manipulation of the arch wire in securing the proper application of forces to the teeth as a result of which the maloccluded teeth will be permanently moved into a desired occluded arch.

There exists no scientific method of placing brackets on teeth in a manner which will allow the practioner to ideally finish treatment with a coplanar arch wire having no buccal-lingual steps or other adjustment factors. Attempts have been made to do this by applying certain fixed values which could include arch wire form, widths, preselected torque or buccal-lingual arch wire step values as determined by established standards or means.

Critical assessment of the nature of a random sample of a number of malocclusions will show that individual variation is so great that the only way to achieve ideal orthodontic objectives is to custom construct individual appliances for individual orthodontic cases. It is commonly accepted that there is considerable variation in labial and buccal dental anatomy of teeth. It is further commonly accepted that the labial and buccal surfaces of teeth are curvilinear in nature. It is a commonly accepted procedure for orthodontists to place brackets more occlusively or more gingivally in an attempt to compensate for over bite or open bite correction. Inasmuch as the tooth surfaces are curvilinear, any height change in bracket placement will result in changes in both torque and buccal-lingual dimensions. It is obvious that one could conclude that the possible number of "ideal combinations" would be in the billions and that the stocking of suitable appliances would not involve a practical clinical procedure.

SUMMARY OF THE INVENTION

The present invention relates to a technique in which the slots of the brackets on the patient's teeth upon completion of treatment are oriented to a pattern predetermined in a set of occluded models or master matrix units, the pattern being of coplanar, finite form. When treatment of the patient is completed, the bracket slots will define a coplanar continuum and the teeth will be aligned according to the idealized model.

Two basic methods may be utilized for slot orientation. The first includes securing blank or unslotted brackets in an idealized occlusive pattern in a model and forming slots therein in a common plane and the second relates to adjusting and fixing pre-slotted brackets in a model in the same pattern. The brackets thus slotted are affixed to the patient's teeth in proper position such that upon completion of treatment, the slots will define a single plane and a predetermined arch curvature which corresponds to the shape of the idealized dental arch. Achieving this, the clinician observes that the treatment is completed.

More particularly, the invention relates to a method of orthodontics for correcting malocclusion comprising the steps of securing blank brackets in predetermined position to the teeth, respectively, in a patient's mouth, making an impression of the patient's teeth with the blank brackets in place, removing the blank brackets and placing them in the respective bracket portions in the impression, forming a working cast of the dental arch from the impression with the blank brackets in place, sectioning the teeth from the working cast, securing the cast teeth in a master matrix unit in the desired occlusion, forming coplanar slots in the blank brackets of the master matrix unit with the bases of the slots conjointly defining the arch of a coplanar arch wire of predetermined shape that conforms to the shape for final treatment, replacing the slotted brackets in the respective original positions on the patient's teeth, and attaching an arch wire device to the slotted brackets in the patient's mouth.

Certain apparatus useful for practicing the aforesaid method provides for mounting a bracket in a desired location on a tooth in the patient's mouth by bonding. This apparatus includes a rigid cap having an internal shape conforming to the incisal portion of the tooth, a guiding tube mounted in predetermined position on the cap, and a frame having spaced end portions, one of the end portions being received for rectilinear guiding movement in the guiding tube and the other end portion being adapted to carry thereon a bracket which may be abutted against the side of the tooth upon appropriate movement of the frame in the guide.

It is an object of this invention to provide a more efficient method of orthodontics.

It is a further object to provide a method of orthodontics which will enable a clinician to determine with assurance that the desired treatment is completed.

It is still a further object to provide an apparatus for locating precisely a bracket on a tooth which is to be bonded thereto.

The above-mentioned and other features and objects of this invention and the manner of attaining them will become more apparent and the invention itself will be best understood by reference to the following description of an embodiment of the invention taken in conjunction with the accompanying drawings.

DESCRIPTION OF THE PREFERRED EMBODIMENT

Figure 1:
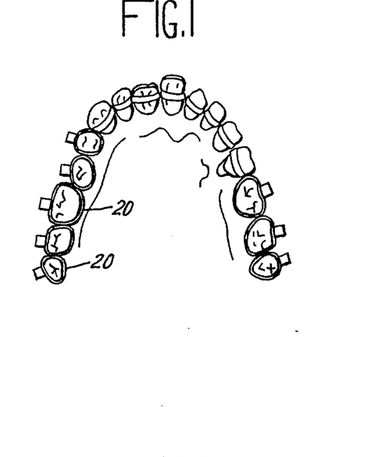
FIG. 1 is a plan view of typical maloccluded teeth in a patient's mouth with bands and blank brackets mounted thereon in accordance with this invention.
Figure 2:
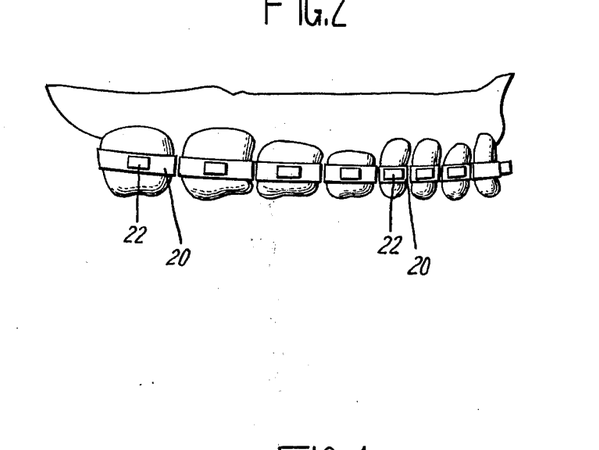
FIG. 2 is a side view thereof.
Figure 3:
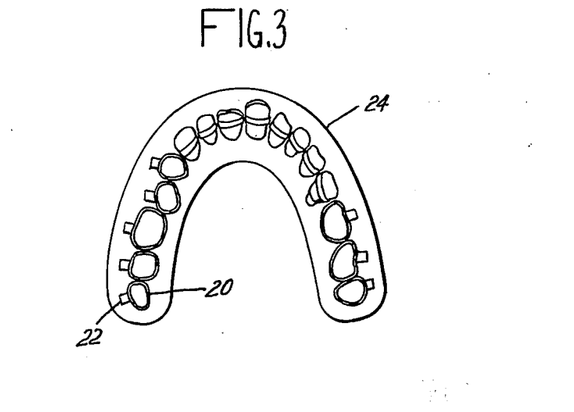
FIG. 3 is a plan view of an impression taken of the dental arch of FIGS. 1 and 2 with the bands and brackets mounted in place.
Figure 4:
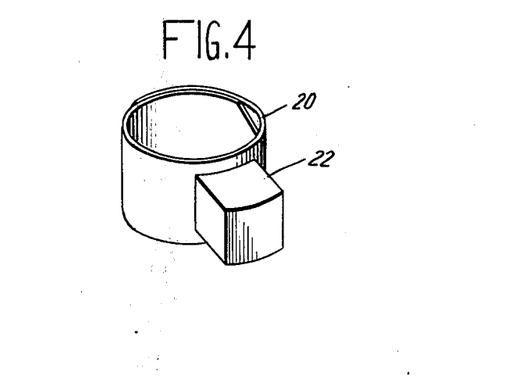
FIG. 4 is a prespective view of a typical band and blank bracket used in practicing the method of this invention.
Figure 5:
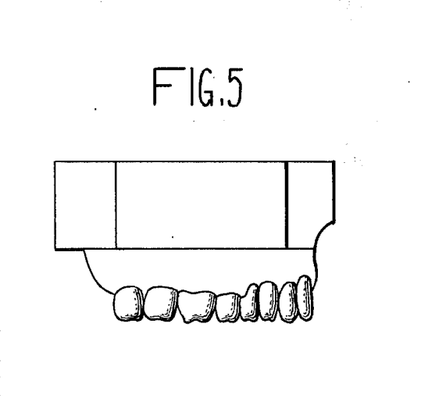
FIG. 5 is a side view of the working cast made from the impression of FIG. 3 having the bands and brackets in place on the working cast.

Referring to the drawings, and more particularly to FIGS. 1 and 2, a typical malocclusion which is to be treated according to this invention is shown. Tooth bands 20 with blank (not slotted) brackets 22 affixed thereto in the usual manner are applied to the teeth in desired position by the clinician. One of the band-bracket combinations 20, 22 is shown in FIG. 4 and is particularly characterized by the absence of any slots or cavities in the bracket 22. An impression 24 (FIG. 3) of the patient's mouth is then taken so as to obtain an impression of the position of the teeth with the bands and brackets attached thereto. The bands and brackets 20, 22 are then inserted into the appropriate tooth cavities in the impression 24. Casting material is poured into the impression 24 with the bands and brackets in place for the purpose of obtaining a working cast or model of the patient's teeth. The cast teeth are then sectioned or separated from the working cast by any suitable method, such as cutting, and reset into a soft plastic media, such as wax, in an ideal or over-treated position as determined by the clinician. The model thus created is in the form of an ideal occlusion or an ideal overtreatment of the original malocclusion as determined by the clinician. Liquid acrylic, for example, is now flowed around the stems of the sectioned teeth, which upon hardening, provides a rigid model of the idealized dental arch which may be handled as an integrated unit, hereinafter referred to as the master matrix unit. Such a master matrix unit is indicated by the numeral 26 in FIG. 6.

Figure 7:
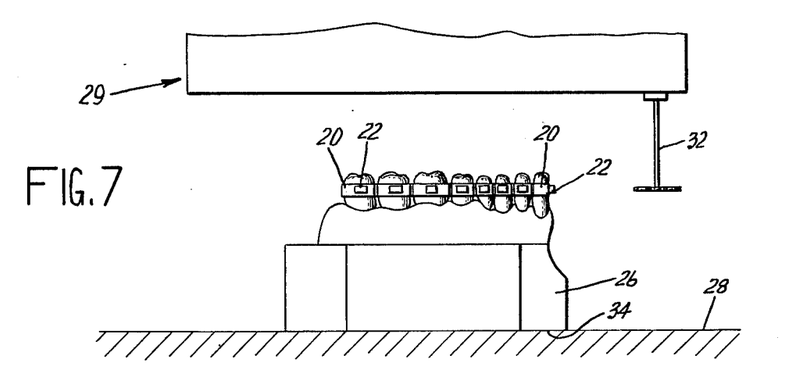
FIG. 7 is a side view of the working cast of FIG. 6 with the bands and blank brackets mounted in place and in position to have slots milled in the brackets.
Figure 8:
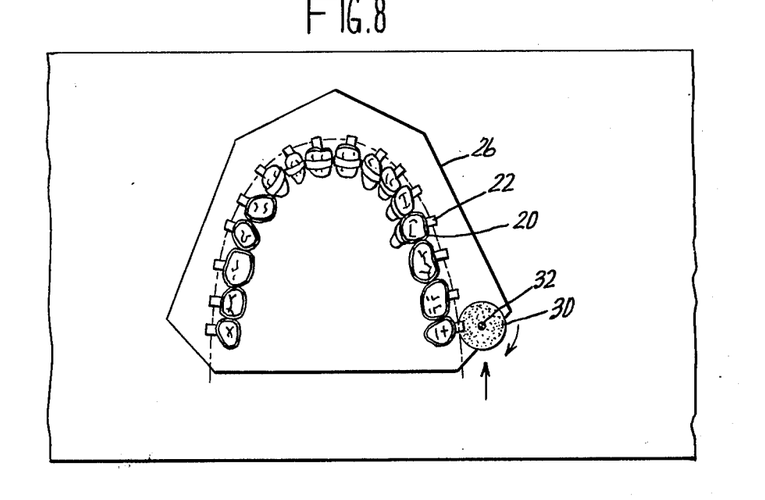
FIG. 8 is a plan view of the working cast of FIG. 7 showing the milling cutter in position to cut slots in the brackets.

The matrix unit 26 is next clamped to the horizontal working surface 28 of a milling machine having a disc-shaped cutting tool 30 mounted on a supporting spindle 32. The milling machine not only causes rotation of the spindle and cutter 32, 30 but also moves the cutter 30 in a plane parallel to the surface 28 in a finite, U-shaped path according to its program. Such milling machines are conventional having continuous path control capable of moving cutter 30 in a precise path automatically.

Prior to mounting the matrix unit 26 in the milling machine, the bands and brackets 20 and 24 are replaced on the cast teeth in the precise positions as determined by the impression 24 made from the patient's mouth. The undersurface 34 of the matrix unit 26 is machined flat so as to define a plane substantially parallel to a plane that passes through all the brackets 22.

Figure 6:
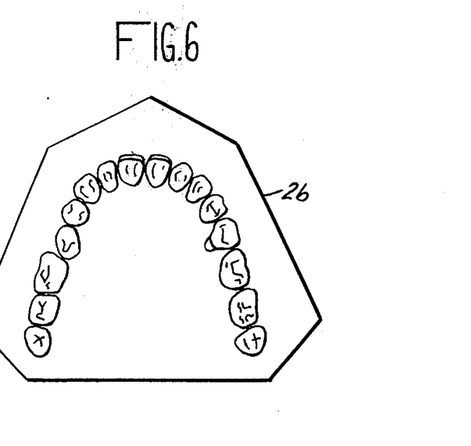
FIG. 6 is a plan view of a matrix unit of cast teeth reset in an occluded arch.

Alternatively, the bands and brackets are retained on the working cast as removed from the impression, and remain on the sectioned replicas as positioned in the matrix unit 26. Also, an impression may be made of the patient's teeth without appliances thereon, a working cast made from this impression and after sectioning, the replicas placed in the master matrix unit. Bands and blank or preslotted brackets may now be applied to the sectioned teeth prior to the operations which are explained later.

Figure 9:
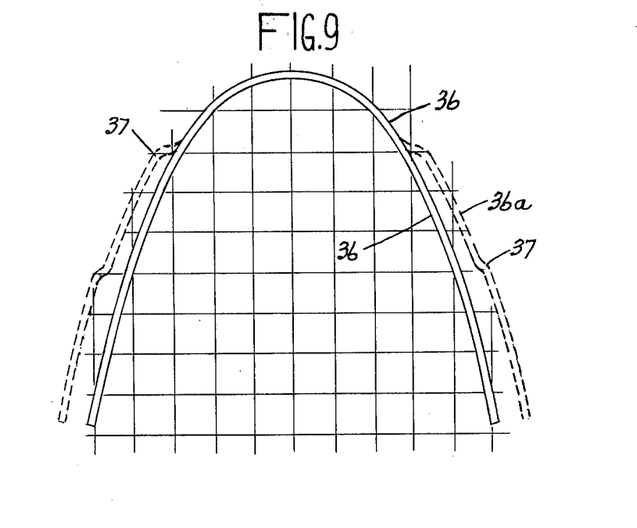
FIG. 9 is a plan view of an arch wire pattern shaped to fit the slots of the brackets in the matrix unit of FIG. 8 after they are formed.
Figure 10:
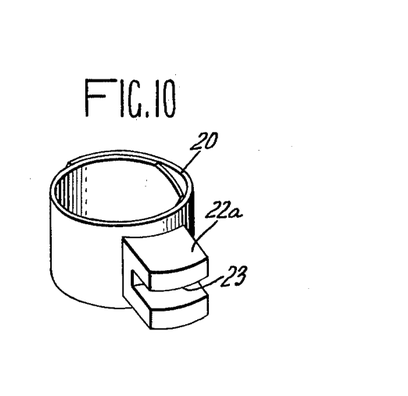
FIG. 10 is a perspective view like FIG. 4 but with the bracket slotted.
Figure 11:
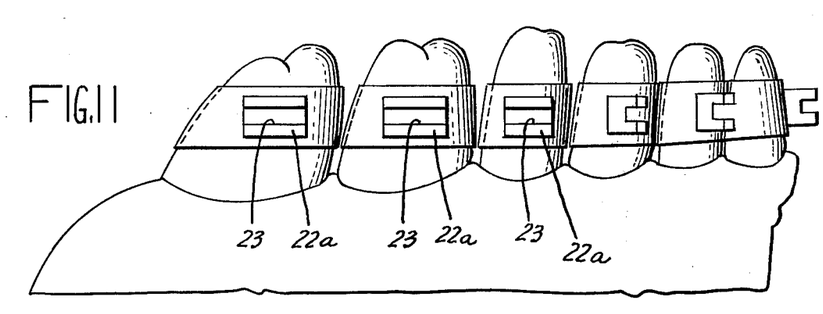
FIG. 11 is a side view of the matrix unit with the bands and brackets in place and showing the bracket slots to be coplanar.

Next, a smoothly curved arch wire pattern as shown in FIG. 9 is determined which will intersect all of the brackets 22 on the matrix unit 26, this pattern being indicated by the numeral 36. This pattern is used to program the milling machine 29 which is then set into operation to cause the cutter 30 to cut through all the brackets 22 in conformity with the pattern 36. This results in each bracket 22 having a slot cut therein, a typical example being shown in FIG. 10 in which a bracket 22a has a slot 23 cut therein. Once the cutting operation is completed, the slots 23 in all the brackets will be coplanar with the bases thereof defining the finite shape of the pattern 36.

Next, an arch wire of rectangular cross-section or some other suitable cross-section as determined by the clinician, will be formed according to the pattern 36 such that it will fit precisely all of the slots in the brackets 22. This pattern 36 and the arch wire are used by the clinician in the treatment of the patient, the arch wire being appropriately fastened to the brackets by means of the slots 23, of course, after the bands and brackets have been replaced in the patient's mouth.

After the milling operation, the bands and brackets are removed from the teeth castings on the matrix unit 26 and replaced in the patient's mouth in the precise positions they were originally. The clinician either uses the arch wire previously described or one formed specially as a part of the overall treatment. Initially it may be preferred to use a wire form such that only a small amount of force is applied to the various teeth and then later to use differently formed wires to alter the force applied as the treatment continues. Eventually, as the teeth approach the occlusion of the idealized model of FIG. 6, the final treatment will be with the arch wire configured according to the shape of the pattern 36 (FIG. 9).

When the teeth are eventually moved to the corrected positions of the matrix unit 26, the slots 23 will be aligned in a common plane with a continuum of the bases scribing an imaginary pattern corresponding precisely to the curvature of the pattern 36. Once this result is achieved, the clinician knows that the teeth have been correctly positioned and that the treatment is finished.

In resetting the teeth in the matrix unit, the clinician may in some cases prefer to position them to correspond to an ideal overtreatment. Thus, again when the slots 23 become aligned as explained, the teeth will reside in overtreated position to the desired extent. Thus, after removal of the orthodontic appliances the teeth will naturally tend to return to a position corresponding to the ideal occlusion.

The shape of the coplanar arch wire slot formed as shown in FIG. 8 need not be smoothly curvilinear according to the pattern 36 of FIG. 9, but alternatively may be conventionally laterally stepped according to the pattern 36a shown partially dashed in FIG. 9. This stepped configuration of the bracket slot continuum is cut by the milling machine 29 (FIG. 7) upon being programmed according to the pattern 36a. Thus, an arch wire formed like the pattern 36a and the path followed by the cutter 30 will precisely fit the slot continuum.

A number of steps 37, as determined by the practioner, typically maxillary lateral incisor and mandibular cuspid and molar steps, may be provided in the applicance to relieve buccal-lingual bulk. This can render the appliance more comfortable and minimize soft tissue irritation.

Orthodontists typically vary the occlusal-gingival height of brackets on teeth, the mesial-distal placement, bracket inclination and angulation. These are mutually interdependent and coupled with variation in dental anatomy render fixed value or stylized appliance therapy, as disclosed, for example, in prior art patents such as Andrews U.S. Pat. Nos. 3,477,128 and 3,660,900, inadequate or ineffective. Such fixed value or stylized appliances, prefabricated without regard to an individualized case, are to be contrasted with the custom fabricated appliances of this invention for each case individually.

In this invention, the bracket slot continuum formed as shown in FIGS. 7 and 8 is coplanar, being alternatively smoothly curvilinear as at 36 (FIG. 9) or stepped as at 36a as may be desired.

Figures 12, 13, 14, 15, 16:
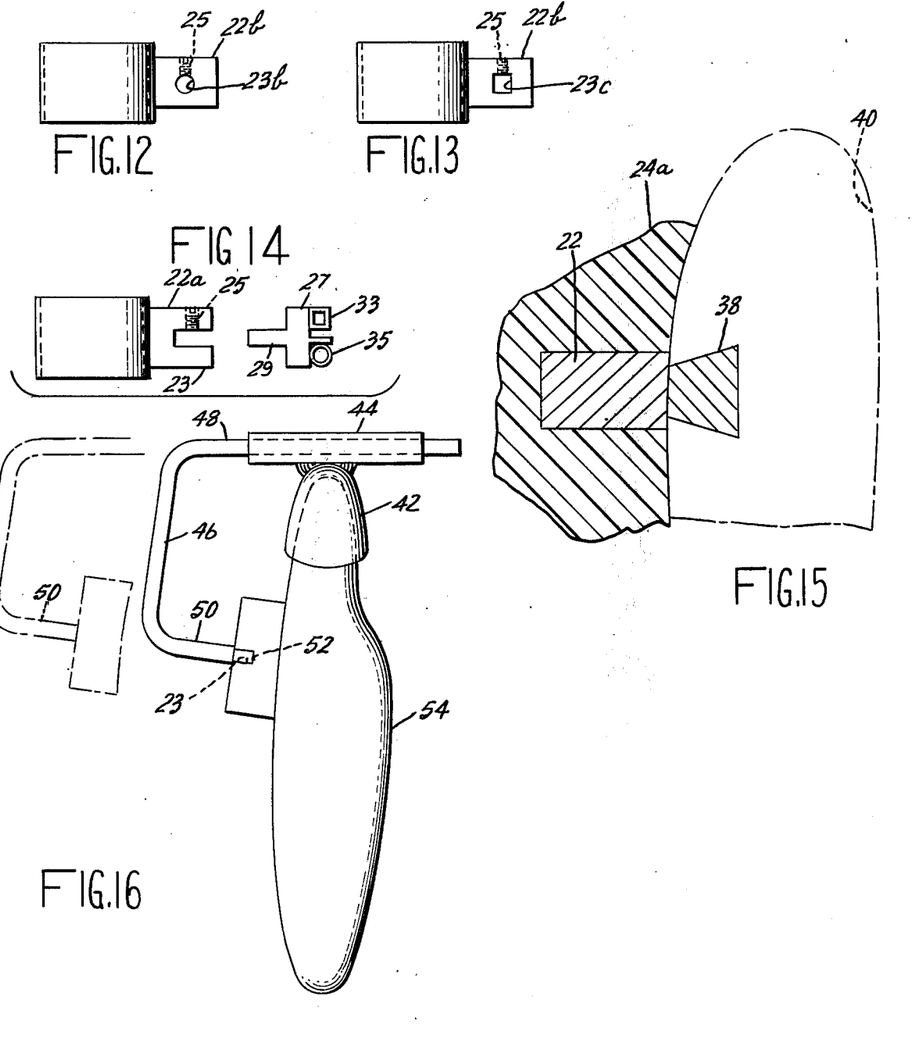
FIGS. 12, 13 and 14 are side views of bands and brackets provided with different forms of attaching cavities to which buccal tubes or attachments may be affixed.
FIG. 15 is a fragmentary, partially sectioned view of one step in the method of making a working cast from an impression which involves the technique of direct bonding a bracket to a tooth in precise position.
FIG. 16 is a side view of an apparatus used in locating a slotted bracket in precise position on a tooth for bonding thereto.

The method of this invention also lends itself to the bonding of brackets directly to the teeth in the conventional manner. In following this method, the blank brackets are initially mounted on a tooth by means of temporary cementing material. Conventional cementing material is used. An impression is made of the patient's mouth, the impression is removed, and the brackets removed from the patient's teeth are inserted in the impression. However, before inserting the brackets into the appropriate cavities in the impression, keystone-shaped anchors 38 are secured to the bases of the blank brackets 22 such that they project into the tooth cavity 40 of the impression 24a as shown in FIG. 15. Thus, when the impression is filled with casting material, the anchors 38 will be firmly embraced thereby securing the blank brackets 22 to the working cast.

As before, the cast teeth are sectioned and then reset and secured in the master matrix unit in which the cast teeth are arranged in the shape of an ideal occlusion (see FIG. 6).

Slots are milled in the brackets as previously explained, and the slotted brackets 22a are then removed from the respective anchors 38. The slotted brackets are then replaced in the patient's teeth and secured with more permanent cement in the same position as originally set.

To achieve the precise setting of the slotted bracket 22a on each tooth, reference is made to FIG. 16 wherein a locating apparatus useful in practicing the method of this invention is shown. At the time the blank brackets 22 are temporarily adhered to the teeth, plastic caps 42 are formed over the incisal portions of the teeth. To each cap 42 is secured an elongated tube 44 in substantially horizontal position. A bent wire frame 46 has an end portion 48 telescopically received within the tube 44. The frame 46 is provided with another end portion 50 having a rectangular projection 52 on the distal end shaped to fit within the slot 53 of the bracket 22a.

When the bracket 22a is originally temporarily secured to the tooth 54, the cap 42 with its tube 44 and frame 46 are so formed and adjusted to register the end of the projection 52 with the intended location of the slot 23. Thus, in replacing the slotted bracket 22a on the tooth 54 in its precise original position, all that need be done is to first remove the frame 46 from the tube 44, fit the slot 23 of the bracket 22a over the projection 52, mount the cap 42 on the incisal portion of the tooth 54 (the internal contour of the cap 42 precisely fitting the incisal edge of the tooth 54) and then inserting the end portion 48 into the tube 44 while holding the cap 42 rigidly on the tooth 54. This will result in the bracket 22a being moved in a direction substantially normal to the plane of the supporting side of the tooth until it contacts the same position as originally set. By applying the cementing material on the back side of the bracket 22a before contacting the tooth 54, once the contact is established, the bracket 22a will be adhered in place.

Following this, the cap 42a and its frame 46 are merely lifted off the tooth.

Since the bracket 22a needs to be both translationally and rotationally located with respect to the tooth 54, it is preferred that the frame wire 46 be of rectangular cross-section as well as the internal passage of the tube 44. Thus, as the frame 46 is moved toward the tooth 54, it will be in its proper rotational position.

The method of this invention may be embodied in still further variation which involves the use of pre-slotted brackets. In this instance, the bands minus the brackets are mounted on the patient's teeth and an impression is taken as before. A working cast is made from the impression with the bands in place, the teeth are sectioned and reset and secured in a master matrix unit. Since the bands are in place on the cast teeth, they need no adjustment. Pre-slotted brackets are now placed and secured on the respective bands with the slots thereof coplanar and defining a previously configured arch wire that conforms to an ideal case. In this connection, based on the desired arch of the cast teeth in the master unit, the clinician forms a coplanar arch wire to the desired finished shape as will resemble the pattern 36 of FIG. 9. The arch wire will then be fitted in the slots of the various brackets and then juxtaposed with respect to the bands in the proper, final treatment position. This arch wire thus serves to position the brackets with respect to the bands. The brackets are now secured to the bands by any suitable means, such as soldering, following which the bands are removed from the cast teeth and replaced in the patient's mouth. The remaining treatment is as explained previously, with finished treatment resulting in all the slots being coplanar and defining an arch form corresponding to the predetermined "ideal case".

Instead of the pre-slotted brackets being separate from the bands and thereafter attached as just described, a swivel attachment may be used. Upon adjustment while on the master matrix unit, the brackets are aligned as previously described with the slots coplanar and the swivel attachments made rigid, such as by fusing or soldering.

If it is desired to utilize some form of buccal attachment, bands and brackets configured like those shown in FIGS. 12, 13 and 14 may be used. In FIG. 12, a specially made bracket 22b has a cylindrical, buccal tube opening 23b formed therein. A threaded opening 25 receives a setscrew for securing a buccal tube in the bore 23b.

In FIG. 13, the bracket 2b has a bore 23c of square cross-section instead of cylindrical as shown in FIG. 12. In FIG. 14, the bracket 22a has the slot 23 as previously explained formed therein but is provided with a threaded opening 25 for receiving a setscrew. A buccal tube attachment of generally elongated and rectangular configuration has a projection 29 adapted to fit snuggly into the slot 23. Suitable buccal tubes 33 and 35 are secured by soldering or the like to the outer face of the attachment 27 such that when the projection 29 is fitted into the slot 23 and there secured by means of a setscrew in the threaded opening 25, the attachment 27 and the buccal tubes 33 and 35 will be securely locked into position. It will thus be seen that the present invention lends itself to a complete set of appliances for use in the full treatment of malocclusion.

A generic concept of this invention is to form brackets with slots properly oriented to be coplanar and to conform to the configuration of an ideal, finally treated dental arch by the technique of forming the slots in blank brackets after they are located in a simulated occlusion or preslotted blanks are positioned and then secured with the same relative orientation. In the treatment process, both methods will result in the slots becoming coplanar when the teeth have been positionally corrected. When the slots become coplanar and the final arch wire in the form of the master pattern fits the slots without deflection, the clinician knows that the treatment is completed.

While there have been described above the principles of this invention in connection with specific apparatus, it is to be clearly understood that this description is made only by way of example and not as a limitation to the scope of the invention.

What is claimed is:

1. A method of orthodontics for correcting malocclusion comprising the steps:
   a. securing blank brackets in predetermined position to the teeth, respectively, in a patient's mouth,
   b. making an impression of the patient's teeth with the blank brackets in place,
   c. removing the blank brackets from the patient's mouth and placing them in the respective bracket portions in the impression,
   d. forming a working cast from the impression with the blank brackets in place,
   e. sectioning the teeth from the working cast, securing said cast teeth in a master matrix unit in the desired occlusion thereof,
   f. forming arch wire slots in said blank brackets mounted on the cast teeth in positions corresponding to the original positions on the patient's teeth while secured to said matrix unit in predetermined locations,
   g. replacing said slotted brackets onto the patient's teeth in the original positions thereof, and
   h. attaching an arch wire device to said brackets.

2. The method of claim 1 wherein said blank brackets are secured to said cast teeth at the time of making the working cast, the sectioned teeth thereby having the blank brackets thereon at the time of securing them into the matrix unit.

3. The method of claim 1 in which said slots when formed in the brackets on said matrix unit are coplanar and have bases that conjointly conform to a coplanar arch wire shaped to correspond to that desired for final treatment.

4. The method of claim 1 in which the step of slotting said brackets includes cutting said slots to a conjoint pattern that is coplanar and conforms to the curvature of a predetermined arch wire pattern as desired for final treatment.

5. The method of claim 1 in which the blank brackets are originally secured to the patient's teeth by means of bands, said working cast being made with the bands and brackets positioned in said impression, said bands and brackets being on the cast teeth of said matrix unit during formation of said slots.

6. The method of claim 1 in which the blank brackets are temporarily secured to the patient's teeth, are removed therefrom and placed in said impression, anchoring said blank brackets to said working cast at the time it is formed, and said replacing step including removing the slotted brackets from the matrix unit and directly securing them in the original positions in the patient's mouth.

7. The method of claim 4 wherein said step of cutting includes milling said slots by moving said matrix unit relative to a milling cutter in conformity with the curvature of said arch wire pattern.

8. The method of claim 4 wherein said blank brackets are originally secured to the patient's teeth by means of bands, said working cast being made with the bands and brackets positioned in said impression, said bands and brackets being on the cast teeth of said matrix unit during formation of said slots.

9. In a method of orthodontics the steps comprising
   a. affixing blank brackets in predetermined position to the teeth, respectively, in a patient's mouth,
   b. securing said blank brackets in a dental arch configuration corresponding to a desired ideal occlusion of the patient's teeth,
   c. forming coplanar slots in the blank brackets to an arch wire pattern of predetermined shape,
   d. replacing the slotted brackets in the respective original positions on the patient's teeth, and
   e. attaching an arch wire device to said slotted brackets in the patient's mouth.

10. A method of orthodontics for correcting malocclusion comprising the steps:
   a. securing blank brackets in predetermined position to the teeth, respectively, in a patient's mouth,
   b. making an impression of the patient's teeth with the blank brackets in place,
   c. removing the blank brackets and placing them in the respective bracket portions in the impression,
   d. making a working cast of the dental arch from said impression and securing said blank brackets in position on the cast teeth thereof corresponding to the original position on the patient's teeth,
   e. sectioning the cast teeth with the blank brackets thereon from the working cast,
   f. positioning and securing the cast teeth with the blank brackets thereon in the desired ideal location in a master matrix unit,
   g. forming coplanar slots in the blank brackets of the master matrix unit with the bases of the slots conjointly defining the curvature of a coplanar arch wire of predetermined shape that conforms to the shape for final treatment,
   h. replacing the slotted brackets in the respective original positions on the patient's teeth, and i. attaching an arch wire device to said slotted brackets in the patient's mouth.

11. The method of claim 3 in which the configuration defined by the bases of said slots is smoothly curvilinear.

12. The method of claim 3 in which the configuration defined by the bases of said slots includes lateral steps.

13. The method of claim 9 in which said predetermined arch wire shape is smoothly curvilinear.

14. The method of claim 9 in which said predetermined arch wire shape is laterally stepped.

15. The method of claim 10 in which the predetermined arch wire shape is smoothly curvilinear.

16. The method of claim 10 in which the predetermined arch wire shape contains lateral bends.

17. In a method of orthodontics the steps comprising
a. securing blank brackets in a dental arch configuration corresponding to a desired occlusion of the patient's teeth in which said blank brackets are arranged substantially in a common plane,
b. forming slots in the blank brackets in which said slots are coplanar and conjointly conform to an arch wire pattern of predetermined shape,
c. placing the slotted brackets on the patient's teeth in predetermined positions corresponding to the positions thereof in said dental arch configuration, and
d. attaching an arch wire device to said slotted brackets, said arch wire device being of a shape corresponding to said predetermined shape.

18. The method of claim 17 in which the step of securing the blank brackets in said dental arch configuration includes making a working cast of the maloccluded teeth of the patient's mouth, said working cast containing replicas of the patient's teeth, sectioning the cast replicas from the working cast, positioning and securing the cast replicas in the desired ideal location in a master matrix unit, and securing said blank brackets onto predetermined ones of the cast replicas of said matrix unit in substantially coplanar arrangement.

19. The method of claim 18 in which said slotted brackets are placed on the patient's teeth in the same corresponding positions as they were positioned on said cast replicas, repectively.

20. The method of claim 15 in which the step of forming a master matrix unit includes making an impression of the patient's maloccluded teeth, forming a working cast from the impression, said working cast containing replicas of the patient's teeth, sectioning the replicas from the working cast, and rigidly securing said replicas in a master matrix unit.

21. The method of claim 20 in which the steps of providing brackets on said replicas includes the steps of securing blank brackets to said replicas in a substantially coplanar arrangement, forming coplanar slots in said blank brackets while mounted on said master matrix unit, said coplanar slots conjointly defining the curvature of a coplanar arch wire.

22. The method of claim 21 wherein the step of affixing the slotted brackets to the patient's tooth includes the steps of removing the slotted brackets from said replicas, and securing the slotted brackets to the patient's teeth in positions corresponding to the positions on the respective replicas.

23. The method of claim 22 wherein the step of fastening the arch wire device to the brackets in the patient's mouth includes the steps of forming an arch wire to the aforesaid coplanar arch wire curvature, and fitting the arch wire to the slots in the brackets as mounted on the patient's teeth.

24. The method of claim 23 wherein the steps of forming said coplanar slots and arch wire include the steps of forming the conjoint shape of the slots and arch wire irregularly with matching maxilary lateral incisor and mandibular cuspid and molar steps.

25. The method of claim 23 wherein the steps of forming said coplanar slots and arch wire include the steps of forming the conjoint shape of the slots and arch wire with lateral steps.

26. The method of claim 23 wherein the steps of forming said coplanar slots and arch wire include the steps of forming the conjoint shape of the slots and arch wire smoothly curvilinear.

27. The method of claim 21 wherein the blank brackets are mounted on bands and the bands are fitted to the replicas whereby such bands will fit the respective teeth in the patient's mouth.

28. In a method of orthodontics the steps comprising rigidly securing a multiplicity of blank brackets in predetermined relative locations, forming slots in the blank brackets according to a predetermined geometric configuration, which configuration corresponds to a predetermined shape of an arch wire, the aforesaid slots when located in a dental arch configuration corresponding to a desired occlusion of a patient's teeth conforming to said predetermined shape.

29. The method of claim 28 wherein said blank brackets are secured in a dental arch configuration corresponding to a desired occlusion of the patient's teeth, said slots being formed in the blank brackets in a pattern corresponding to said predetermined arch wire shape, placing the slotted brackets on the patient's teeth in the predetermined positions corresponding to the positions of said blank brackets in said dental arch configuration, and attaching an arch wire device to said slotted brackets, said arch wire device being of a shape corresponding to said predetermined shape.

30. The method of claim 29 in which the step of securing the blank brackets in said dental arch configuration includes making a working cast of the maloccluded teeth of the patient's mouth, said working cast containing replicas of the patient's teeth, sectioning the cast replicas from the working cast, positioning and securing the cast replicas in the desired ideal location in a master matrix unit, and securing said blank brackets onto predetermined ones of the cast replicas of said matrix unit.

31. Apparatus for mounting a bracket in a desired location on a tooth in a patient's mouth comprising a rigid cap having an internal shape conforming to the shape of the incisal edge of a tooth, a carrier having a bracket-supporting portion thereon, means on said cap cooperable with said carrier for movably guiding said bracket-supporting portion in a direction transverse to the tooth axis to a predetermined position corresponding to a location on the tooth to which a bracket is to be fastened, said carrier including a frame having spaced end portions, said means including a guide member on said cap which movably receives one of said end portions, the other end portion carrying said bracket-supporting portion, said guide member including an elongated tube having a bore of non-circular cross-section, said one end portion being received by said elongated tube for rectilinear movement and having a complementary cross-section, and said bracket-supporting portion being in the form of a projection of predetermined shape to fit the slot of a bracket.

* * * * *

UNITED STATES PATENT OFFICE
CERTIFICATE OF CORRECTION

Patent No. 4,014,096  Dated March 29, 1977

Inventor(s) Eugene L. Dellinger

It is certified that error appears in the above-identified patent and that said Letters Patent are hereby corrected as shown below:

IN THE ABSTRACT

Line 7,    "position" should read -- positions --.

Claim 20, Column 9, lines 45 to 51:

"20. The method of claim 15 in which the step of forming a master matrix unit includes making an impression of the patient's maloccluded teeth, forming a working cast from the impression, said working cast containing replicas of the patient's teeth, sectioning the replicas from the working cast, and rigidly securing said replicas in a master matrix unit."

should be:

--20. In a method of orthodontics the steps comprising forming a master matrix unit containing rigidly secured replicas of a patient's maloccluded teeth located in an ideal occlusion, providing brackets on said replicas with slots and with the slots coplanar, removing said brackets from said replicas and affixing them to the patient's teeth in the same locations as correspond to the locations on said replicas, fastening an arch wire device to the brackets in the patient's mouth; the step of forming a

UNITED STATES PATENT OFFICE
CERTIFICATE OF CORRECTION

Patent No. 4,014,096    Dated    March 29, 1977

Inventor(s)    Eugene L. Dellinger

It is certified that error appears in the above-identified patent and that said Letters Patent are hereby corrected as shown below:

master matrix unit including making an impression of the patient's maloccluded teeth, forming a working cast from the impression, said working cast containing replicas of the patient's teeth, sectioning the replicas from the working cast, and rigidly securing said replicas in a master matrix unit.--

Claim 28, Column 10, line 27 "occlusion" should be --arrangement--

Signed and Sealed this

Twentieth Day of September 1977

[SEAL]

Attest:

RUTH C. MASON
Attesting Officer

LUTRELLE F. PARKER
Acting Commissioner of Patents and Trademarks